(12) United States Patent
Schneider et al.

(10) Patent No.: US 8,869,753 B2
(45) Date of Patent: Oct. 28, 2014

(54) EFFECTS OF BIODIESEL FUEL ON FUEL DILUTION OF ENGINE OIL

(75) Inventors: Matthew Allen Schneider, Aachen (DE); Yasser Mohamed sayed Yacoub, Cologne (DE); Mario Balenovic, Waalre (NL)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 13/618,286

(22) Filed: Sep. 14, 2012

(65) Prior Publication Data

US 2013/0013177 A1 Jan. 10, 2013

Related U.S. Application Data

(63) Continuation of application No. 12/862,122, filed on Aug. 24, 2010, now Pat. No. 8,302,578.

(30) Foreign Application Priority Data

Oct. 28, 2009 (DE) .......................... 10 2009 046 075

(51) Int. Cl.
*F02B 75/12* (2006.01)
*G01N 33/28* (2006.01)

(52) U.S. Cl.
CPC ................................. *G01N 33/2817* (2013.01)
USPC ................................ 123/1 A; 60/277; 60/285

(58) Field of Classification Search
USPC ...... 123/1 A, 196 R, 198 R; 60/277, 285, 286, 60/303; 73/53.01, 53.05
See application file for complete search history.

(56) References Cited

U.S. PATENT DOCUMENTS

| 4,421,078 | A  | * | 12/1983 | Hurner ...................... 123/196 R |
| 4,495,909 | A  | * | 1/1985  | Hurner ...................... 123/196 R |
| 5,035,512 | A  | * | 7/1991  | Tateishi et al. ................. 374/142 |
| 5,067,455 | A  | * | 11/1991 | Okajima et al. .......... 123/196 R |
| 5,687,687 | A  | * | 11/1997 | Trueblood et al. .......... 123/196 S |
| 6,938,585 | B2 | * | 9/2005  | Schneider ...................... 123/1 A |
| 7,739,904 | B2 | * | 6/2010  | Yokoi et al. ................. 73/114.56 |
| 8,087,233 | B2 | * | 1/2012  | Yokoi et al. ..................... 60/285 |
| 8,302,578 | B2 | * | 11/2012 | Schneider et al. ......... 123/196 R |
| 2009/0145211 | A1 |  | 6/2009 | Schneider |

FOREIGN PATENT DOCUMENTS

| DE | 102004039836 A1 | 3/2006 |
| DE | 102005051924 A1 | 5/2007 |
| DE | 102007054858 A1 | 5/2009 |

OTHER PUBLICATIONS

German Search Report dated Jun. 7, 2010, pp. 1-2.

* cited by examiner

*Primary Examiner* — John Kwon
(74) *Attorney, Agent, or Firm* — Brooks Kushman P.C.; Julia Voutyras

(57) ABSTRACT

An engine and related control system determine an amount of fuel diluting the engine oil in the oil pan. Such information can be used to recommend an oil change and to estimate a fraction of biodiesel in the fuel supplied to the engine. According to one embodiment, actual oil volume in the oil pan is based on a signal from a level sensor in the oil and a theoretical oil volume is determined based on initial oil volume and fuel entering the oil in the oil pan, fuel leaving the oil pan due to evaporation, and oil being consumed in the combustion chamber. Based on the difference between the actual and theoretical oil volumes, a proportion of heavy fuel components or biodiesel can be determined and transmitted to an engine control system.

17 Claims, 3 Drawing Sheets

EFFECTS OF BIODIESEL FUEL ON FUEL DILUTION OF ENGINE OIL

CROSS-REFERENCE TO RELATED APPLICATIONS

This application is a continuation of U.S. patent application Ser. No. 12/862,122 filed Aug. 24, 2010 which claims priority benefits under 35 U.S.C. 119(a)-(d) to DE 10 2009 046 075.6, filed Oct. 28, 2009, the disclosures of which are hereby incorporated by reference in their entirety.

TECHNICAL FIELD

The present disclosure relates to dilution of engine oil by fuel in a diesel engine.

BACKGROUND

Fuel injection strategies in modern diesel engines employ post-injection, i.e., injection during the expansion stroke. Such post-injection is used to increase the temperature of exhaust gases and/or to enrich the exhaust gases to regulate the temperature and stoichiometry in a diesel particulate filter or other exhaust aftertreatment device. Some of the fuel is sprayed on cylinder walls and then is scraped by the oil ring on the piston into the crankcase of the engine. Some of the fuel that is carried into the engine oil in the crankcase evaporates, in particular the lighter ends of the fuel. However, the heavier ends of the fuel remain in the oil and accumulate.

Oil dilution by the fuel can cause the level in the oil pan to exceed the maximum permissible level. This can cause excess foaming of the oil due to the crankshaft dipping into the oil during rotation carrying air into the oil. Oil that has foam has degraded lubricating properties and therefore may shorten the service life of the engine. Furthermore, fuel in the oil reduces the oil's viscosity and degrades the oil's resistance to oxidation. In extreme cases, fuel laden oil is carried into the combustion chamber and affects the power produced by the engine. These problems are exacerbated by the heavier components found in diesel fuel, which do not evaporate as quickly as lighter components.

Computational models of oil dilution are used to estimate the rate at which fuel is added to the oil and the rate at which fuel is removed from the oil by evaporation. Such a model assumes diesel fuel. If, however, a biodiesel fuel is used instead, the model's accuracy suffers. The proportion of heavy components in biodiesel fuel is higher than in conventional diesel fuel. As such, the disadvantages associated with engine oil dilution are exacerbated by the increase in the amount of heavy components as the proportion of biodiesel relative to conventional diesel increases.

SUMMARY

A method is disclosed for determining an amount of fuel in the engine oil and the proportion of heavy and light diesel components in the fuel. Such information can be used to recommend an oil change and to estimate a fraction of biodiesel in the fuel supplied to the engine.

The oil volume of the engine oil can be detected by measuring the oil level in the oil pan of the engine and converting it into an oil volume on the basis of the shape of the oil pan, or by a calculation unit in which the shape of the oil pan is stored. However, the conversion of the oil level into an oil volume may also be determined based on a calibration in which volume in the oil pan is determined as a function of height.

A method for determining a proportion of heavy diesel components in fuel diluting engine oil in a diesel engine, includes: detecting an oil volume in an oil pan coupled to the diesel engine, calculating a theoretical oil volume in the oil pan determining a difference between the detected and theoretical oil volumes, and estimating the proportion of heavy diesel components in fuel diluting engine oil. The theoretical oil volume is based on oil volume in the oil pan at an initial time, an input rate of fuel into the engine oil, and an evaporation rate of fuel from the engine oil. In one embodiment, the theoretical oil volume is a linear function of time. The detecting the oil volume is based on a signal from a level sensor provided in the oil pan. The oil volume is further based on the shape of the oil pan as a function of height in the oil pan or calibration of volume as a function of height in the oil pan. The method may also include estimating a proportion of biodiesel blended in the fuel supplied to the engine based on the determined proportion of heavy diesel components relative to the composition of traditional diesel. The estimating a theoretical oil volume is based on the fuel supplied to the engine being diesel fuel of an assumed composition. The theoretical oil volume may be further based on oil consumption of the engine. The method may further include transmitting the estimated proportion of biodiesel to an engine control system coupled to the diesel engine. The method may further include recommending an oil change interval based on the proportion of fuel diluting engine oil.

A diesel engine according to an embodiment of the disclosure includes an oil pan with an initial oil volume, a level sensor disposed in the oil pan, and an electronic unit coupled to the level sensor and the engine. The electronic unit: detecs an oil volume based on a signal from the level sensor, calculates a theoretical oil volume in the oil pan, determines a difference between the detected and theoretical oil volumes, and estimates a composition of oil in the oil pan. The electronic unit estimates a proportion of biodiesel blended in the fuel based on the difference between the detected and theoretical oil volumes. The diesel engine also has an engine control system electronically coupled to the electronic unit and the diesel engine wherein the electronic unit transmits the estimated proportion of biodiesel to the engine control system. The electronic control unit may determine the theoretical oil volume based on an initial oil volume and an increase in volume due to fuel diluting oil in the oil pan. The theoretical oil volume may be further based on a decrease in volume due to fuel in the oil pan vaporizing and/or a decrease in oil volume due to oil from the oil pan traveling to a combustion chamber of the engine and being combusted. The theoretical oil volume calculated is based on the fuel being supplied to the engine being diesel fuel of a known composition.

DETAILED DESCRIPTION

As those of ordinary skill in the art will understand, various features of the embodiments illustrated and described with reference to any one of the Figures may be combined with features illustrated in one or more other Figures to produce alternative embodiments that are not explicitly illustrated or described. The combinations of features illustrated provide representative embodiments for typical applications. However, various combinations and modifications of the features consistent with the teachings of the present disclosure may be desired for particular applications or implementations. Those of ordinary skill in the art may recognize similar applications or implementations consistent with the present disclosure, e.g., ones in which components are arranged in a slightly different order than shown in the embodiments in the Figures. Those of ordinary skill in the art will recognize that the teachings of the present disclosure may be applied to other applications or implementations.

Figure 1:
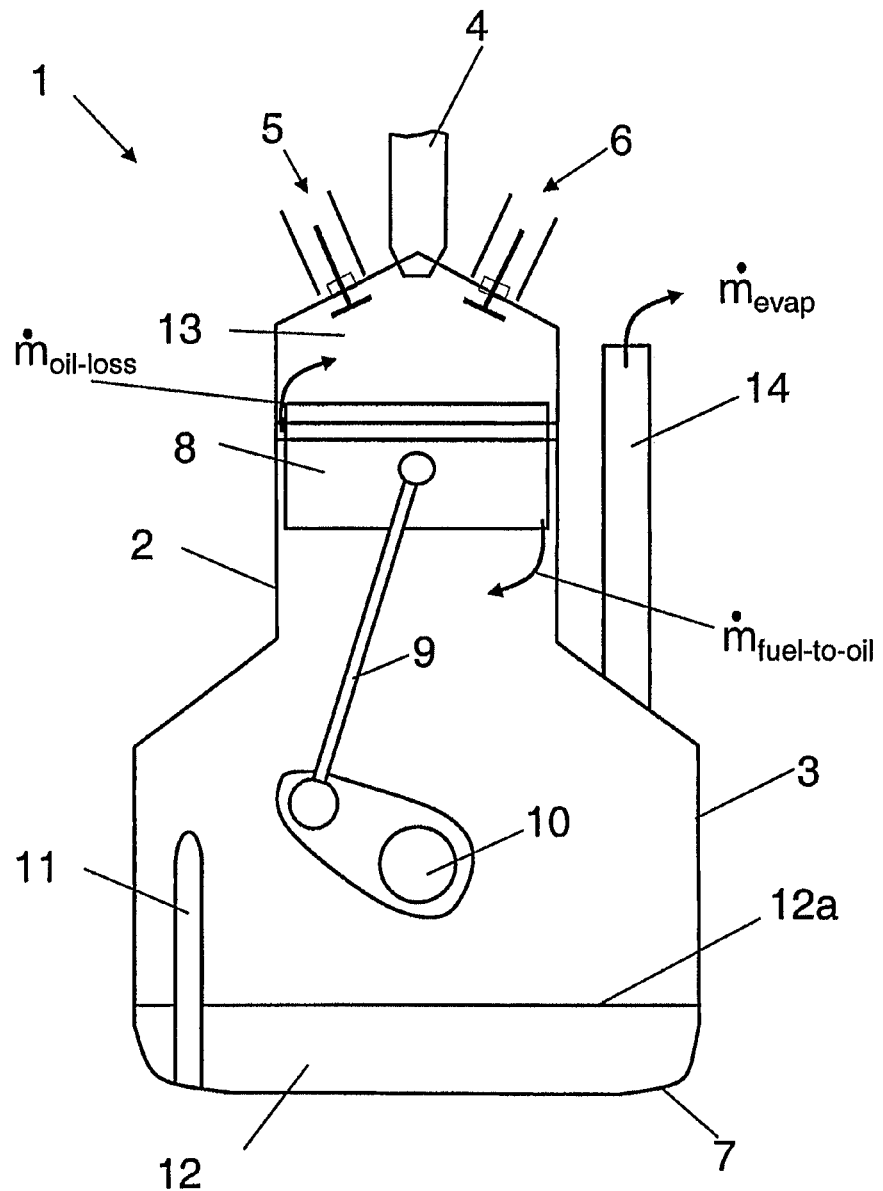
FIG. 1 is a cross-section illustration of a diesel engine.

FIG. 1 shows a schematic cross-sectional illustration of a single cylinder 2 of a diesel engine 1. Typically, the engine has a plurality of cylinders arranged along an axis. A fuel injection nozzle 4, an air inlet valve 5 and an exhaust gas outlet valve 6 are arranged at the upper end of cylinder 2. The lower end of cylinder 2 is adjoined by crankcase 3 onto which an oil pan 7 is provided. A piston 8 reciprocates within cylinder 2. Diesel engine 1 furthermore has a level sensor 11 which detects a level 12a of engine oil 12 in oil pan 7. A signal is transmitted to an electronic module (not illustrated in FIG. 1) as a function of the detected level.

Piston 8 is attached, via a connecting rod 9, to a crankshaft 10 of engine 1. Crankshaft 10 is arranged in crankcase 3. Piston 8 is sealed with respect to cylinder 2 by piston rings. However, the piston rings of piston 8 do seal perfectly and therefore permit a portion of the fuel, $\dot{m}_{fuel\_to\_Oil}$, to pass into crankcase 3, where it dilutes and thins engine oil 12 in oil pan 7, Some of engine oil 12 travels into combustion chamber 13 wherein it is combusted, i.e., lost. Such oil is denoted as $\dot{m}_{Oil\_loss}$.

Fuel entering oil pan 7 does not all accumulate there. Owing to evaporation, the light components of the fuel, $\dot{m}_{evap\_light}$, actually vaporize. Only the heavy, less volatile, components of the fuel accumulate in oil pan 7. Vaporized fuel components can be discharged, together with exhaust gases which have passed into crankcase 3, via a venting duct 14. These gases are not vented to the atmosphere, but may be recirculated to the intake of the engine for combustion.

Compared to conventional diesel fuels, biodiesel has a higher proportion of heavy components. Thus, a lesser fraction of biodiesel vaporizes. If biodiesel is added to a diesel fuel, there is an increase in the proportion of heavy components in the fuel which accumulates in oil pan 7. The proportion of biodiesel in the fuel is generally not known and also varies between various providers of blended diesel fuel. For this reason, the proportion of heavy components contained in the diesel fuel can vary from one refueling to another. An oil change is desired when the oil has been diluted by more than a threshold amount of fuel to avoid the problems described above. If the fuel blend provided to the engine has a high fraction of biodiesel, which has a lesser fraction of lighter ends, the threshold dilution level is reached more quickly. Conversely, if a fuel blend has a higher fraction of fuel with the lighter components, the threshold dilution level is reached after a longer interval and an oil change can be delayed.

The proportion of heavy components in fuel diluting engine oil can be estimated computationally based on the assumption that the fuel is a standard diesel fuel. The actual volume of oil plus fuel in oil pan 7 can be determined based on level sensor 11 based on a relationship of volume as a function of height in oil pan 7, which can be known due to a computation based on oil pan 7 shape or by calibration.

The measured oil volume is compared with the estimated oil volume. If the measured oil volume exceeds the calculated oil volume, fuel dilution containing heavy components exceeding that expected for diesel fuel can be inferred. From this, a proportion of biodiesel fuel blended with diesel fuel can also be inferred.

A model is applied in which a calculated oil volume is determined at a time, t, according to the formula accounting for sources and sinks of the volume in the oil pan:

$$V_{model}(t) = V_{oil}(t = t_0) + \frac{\dot{m}_{fuel\_to\_Oil} \times t}{\rho_{oil}} - \frac{\dot{m}_{evap\_light} \times t}{\rho_{oil}} \quad (1)$$

from the known oil volume $V_{oil}(t=t_0)$ at a starting time $t_0$, the input rate, $\dot{m}_{fuel\_to\_Oil}$, of fuel into the engine oil, the evaporation rate, $\dot{m}_{evap\_light}$, of the light components of the diesel fuel and the density, $\rho_{oil}$, of the diesel fuel which corresponds to the selected target composition. Both the input rate and the evaporation rate are constant over time within the scope of the model used in the exemplary embodiment, which means that a linear relationship results between the calculated oil volume and the time. In the formula above, the oil consumption $$\frac{\dot{m}_{Oil\_loss} \times t}{\rho_{oil}}$$

of the diesel engine can optionally also be taken into account, i.e., a sink for oil. In this case, the appropriate density to use may be the density of oil.

The measured oil volume results from the determined oil level and the known shape of oil pan 7. It can be represented according to the formula $$V_{sensor}(t) = V_{oil}(t=t_0) + V_{Light\_fuel} + V_{heavy\_fuel} \quad (2)$$

as the sum of the oil volume, $V_{oil}(t=t_0)$ at the starting time, $t_0$, the volume, $V_{Light\_fuel}$ of the input light components of the diesel fuel which have not yet evaporated, possibly due to the engine oil not yet attaining a temperature at which the light components evaporate, and the volume, $V_{heavy\_fuel}$, of the input heavy components of the diesel fuel.

Figure 2:
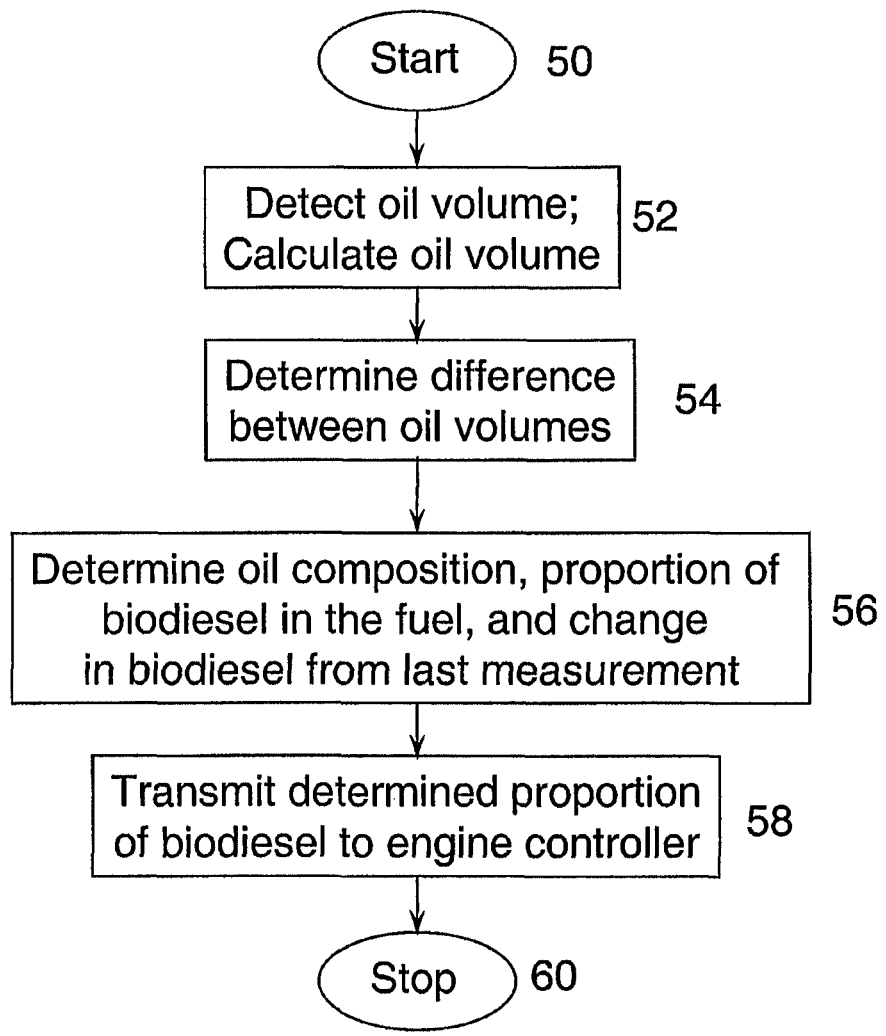
FIG. 2 is a flowchart of a method according to the disclosure.

A flowchart of an embodiment of the method is shown in FIG. 2. The method may be carried out with a stationary diesel engine, i.e., not oil sloshing, after a sufficiently long rest period so that the oil level is at a steady state level. The method starts in 50. In block 52, the oil volume, $V_{sensor}(t)$, is detected based on a signal from the sensor 11. Also, calculated oil volume, $V_{model}(t)$, is determined from the formula above. In 54, the two oil volumes determined in 52 are compared:

$$V_{diff}(t) = V_{sensor}(t) - V_{model}(t)$$
$$= V_{sensor}(t) - V_{oil}(t = t_0) - \frac{1}{\rho_{oil}}(\dot{m}_{fuel\_to\_Oil} - \dot{m}_{evap\_light}) \times t.$$

If the difference is positive, that is to say the measured oil volume, $V_{sensor}(t)$ is higher than the calculated oil volume, $V_{model}(t)$, this means that the proportion of heavy components in the oil is higher than would be expected given a diesel fuel of the assumed composition. If the difference is, on the other hand, negative, that is to say the measured oil volume, $V_{sensor}(t)$ is smaller than the calculated oil volume, $V_{model}(t)$, this means that the proportion of heavy components in the oil is lower than would be expected based on an assumed diesel composition. The content of biodiesel blended in diesel fuel can be estimated or inferred from the difference and also any change in the proportion of biodiesel since the last determination can be evaluated in block 56. Such information is transmitted to the engine controller in block 58. The algorithm is stopped in 60.

Figure 3:
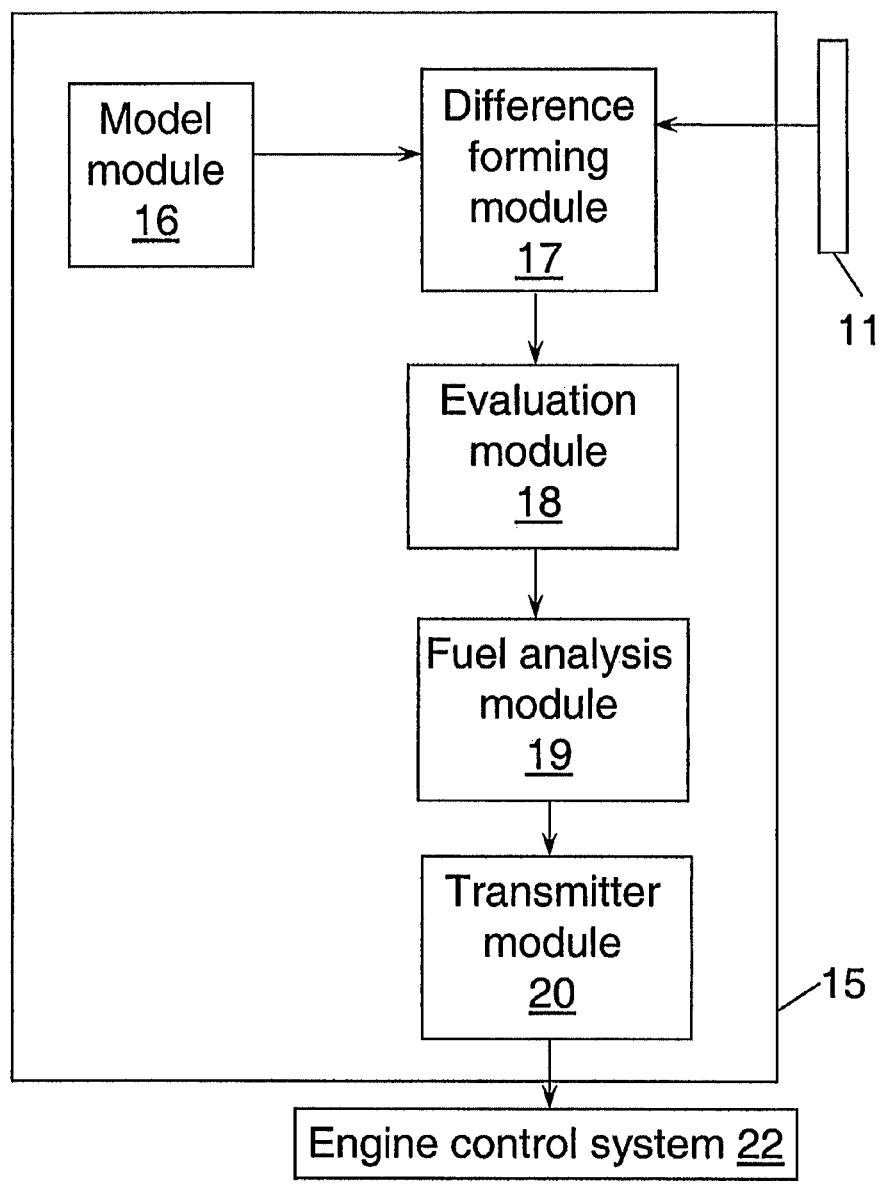
FIG. 3 is a schematic, block diagram of an electronic unit for carrying out a method according to an embodiment of the disclosure.

According to an embodiment of the disclosure, the method can be implemented within the context of an electronic unit in which the method is permanently programmed (ASIC, Application Specific Integrated Circuit), or within the context of a freely programmable electronic unit (CPU, Central Processor Unit), as shown in FIG. 3. A unit 15 is connected to level sensor 11 to receive the level 12*a* of engine oil 12 in oil pan 7. Furthermore, unit 15 contains a model module 16 in which the calculated oil volume is determined on the basis of a model, for example on the basis of the model explained above. A difference-forming model 17 is connected to the model 16 module to receive the calculated oil volume, $V_{model}(t)$. Furthermore the difference-forming module 17 is also connected to the level sensor 11 to receive the measured oil volume, $V_{sensor}(t)$. Difference-forming module 17 determines $V_{diff}(t)$ between the measured oil volume, $V_{sensor}(t)$ and the calculated oil, volume $V_{model}(t)$. An evaluation module 18 that is connected to the difference-forming module determines the oil composition of the engine oil. It is optionally possible, as illustrated in FIG. 3, for there to be a fuel analysis module 19 which is connected to the evaluation module 18 to receive the oil composition of the engine oil, and that determines the proportion of biodiesel in the diesel fuel from the received oil composition. The proportion which is determined can then be passed on to a transmitter module 20, which is connected to the fuel analysis module 19 and which transmits the determined proportion of biodiesel to the engine control system 22. Electronic unit 15 can be embodied, as described with reference to FIG. 3, as an independent unit of a diesel engine or as a subunit of an engine control device.

While the best mode has been described in detail, those familiar with the art will recognize various alternative designs and embodiments within the scope of the following claims. Where one or more embodiments have been described as providing advantages or being preferred over other embodiments and/or over prior art in regard to one or more desired characteristics, one of ordinary skill in the art will recognize that compromises may be made among various features to achieve desired system attributes, which may depend on the specific application or implementation. These attributes include, but are not limited to: cost, strength, durability, life cycle cost, marketability, appearance, packaging, size, serviceability, weight, manufacturability, ease of assembly, etc. The embodiments described as being less desirable relative to other embodiments with respect to one or more characteristics are not outside the scope of the disclosure as claimed.

What is claimed is:

1. A diesel engine, comprising:
an oil pan;
a level sensor disposed in the oil pan; and
an electronic unit coupled to the level sensor and the engine, the electronic unit:
detecting an oil volume based on a level sensor signal, calculating a theoretical oil volume in the oil pan, determining a difference between the detected and theoretical oil volumes, and estimating a proportion of heavy diesel components in fuel diluting the engine oil.

2. The diesel engine of claim 1 wherein the electronic unit estimates a proportion of biodiesel blended in the fuel based on the difference between the detected and theoretical oil volumes.

3. The diesel engine of claim 2, further comprising:
an engine control system electronically coupled to the electronic unit and the diesel engine wherein the electronic unit transmits the estimated proportion of biodiesel to the engine control system.

4. The diesel engine of claim 1 wherein the electronic control unit determines the theoretical oil volume based on an initial oil volume and an increase in volume due to fuel diluting oil in the oil pan.

5. The diesel engine of claim 4 wherein the electronic control unit determines the theoretical oil volume further based on a decrease in volume due to fuel in the oil pan vaporizing.

6. The diesel engine of claim 4 wherein the electronic control unit determines the theoretical oil volume further based on a decrease in oil volume due to oil from the oil pan traveling to a combustion chamber of the engine and being combusted.

7. The diesel engine of claim 1 wherein the theoretical oil volume is calculated based on the fuel being supplied to the engine being diesel fuel.

8. The diesel engine of claim 1 wherein the theoretical oil volume is calculated based on the fuel being supplied to the engine being diesel fuel of a known composition.

9. A control system for a diesel engine having an oil pan with a level sensor, comprising:
a controller coupled to the level sensor and the engine that generates an output in response to an estimated proportion of heavy diesel components diluting oil in the oil pan based on a difference between a detected oil volume detected by the level sensor and a theoretical oil volume.

10. The control system of claim 9 wherein the controller determines the theoretical oil volume based on at least a decrease in oil volume due to oil from the oil pan traveling to a combustion chamber of the engine and being combusted.

11. The control system of claim 9 wherein the controller estimates a proportion of biodiesel blended in fuel based at least on the difference between the detected and theoretical oil volumes.

12. The control system of claim 9 wherein the controller determines the theoretical oil volume based at least on a decrease in volume due to fuel in the oil pan vaporizing.

13. The control system of claim 9 wherein the controller estimates a proportion of biodiesel blended in the fuel.

14. The control system of claim 9 wherein the output corresponds to a recommendation to change the oil.

15. An engine, comprising:
an oil pan;
a level sensor associated with the oil pan; and
an electronic unit coupled to the level sensor and configured to generate an output in response to an estimated proportion of heavy fuel components diluting oil in the oil pan, wherein the estimated proportion is determined based on a difference between oil pan fluid volume detected by the level sensor and a calculated oil volume.

16. The engine of claim 15 wherein the electronic unit estimates the proportion of heavy fuel components diluting oil in the oil pan by determining the calculated oil volume based on an initial oil volume adjusted for at least fuel dilution and fuel vaporizing from oil in the oil pan.

17. The engine of claim 16 wherein the calculated oil volume is further determined based on the fuel being supplied to the engine being diesel fuel.

* * * * *